US007998099B2

(12) United States Patent
Tull et al.

(10) Patent No.: US 7,998,099 B2
(45) Date of Patent: Aug. 16, 2011

(54) METHOD AND APPARATUS FOR BODY WORK

(76) Inventors: Nilda Tull, Arlington, TX (US); William Rich, Arlington, TX (US)

(*) Notice: Subject to any disclaimer, the term of this patent is extended or adjusted under 35 U.S.C. 154(b) by 412 days.

(21) Appl. No.: 12/331,533

(22) Filed: Dec. 10, 2008

(65) Prior Publication Data

US 2010/0139671 A1 Jun. 10, 2010

(51) Int. Cl.
*A61F 5/00* (2006.01)

(52) U.S. Cl. .......................................... 602/17; 128/857

(58) Field of Classification Search .................... 602/17, 602/18; 128/857–858; 2/11, 174, 181.6, 2/DIG. 11

See application file for complete search history.

(56) References Cited

U.S. PATENT DOCUMENTS 1,497,858 A * 6/1924 Lewis ...................... 606/204.35
1,519,016 A * 12/1924 Bellitz .......................... 132/274
1,750,937 A * 3/1930 Morgan ............................ 4/521
2,160,567 A * 5/1939 Sterne ............................... 2/171
2,640,198 A * 6/1953 Mullen ............................. 2/174
4,243,025 A 1/1981 Jones
4,461,286 A 7/1984 Sweat
5,231,977 A 8/1993 Graston
5,366,437 A 11/1994 Graston
5,673,298 A 9/1997 Mazess
5,707,346 A 1/1998 Graston
5,713,816 A 2/1998 Glover
6,126,620 A 10/2000 Graston
6,251,123 B1 6/2001 Patner
6,616,619 B2 9/2003 Fusco
6,730,006 B1 5/2004 Patterson
6,846,270 B1 1/2005 Etnyre
6,971,122 B2 * 12/2005 Sanchez ......................... 2/181.6
7,189,192 B2 3/2007 Edgeton
7,320,668 B1 1/2008 Warder
7,390,286 B1 6/2008 Edgeton
2005/0261616 A1 * 11/2005 Sklar et al. ...................... 602/17
2006/0155220 A1 7/2006 Oslay
2008/0070210 A1 3/2008 Hitzmann
2008/0233549 A1 9/2008 Daniels

OTHER PUBLICATIONS

Informational Pages from Rolf Institute of Structural Integration on Rolfing, massage, yoga, research on Rolfing, answers to questions about Rolfing found at www.rolf.org between Oct. 2008 and Nov. 2008.

* cited by examiner

*Primary Examiner* — Michael A. Brown

(57) ABSTRACT

The present invention provides a method and apparatus for obtaining and maintaining correct alignment of body structure. In one embodiment of the invention, a head band is utilized that places light pressure on the erector spinae and sub occipital muscles below the occiput to relax the muscles that caused the counter clockwise rotation and light pressure is maintained to correct the misalignment of the atlas and occipital condyles. In another embodiment of the invention, the atlas is centered by applying manual gentle pressure to relax the muscles that caused the counter-clockwise rotation. Once relaxed, light pressure is manually applied to correct the misalignment of the atlas and occipital condyles. Gentle pressure can also be applied to the muscles that tightened as a result of the misplaced atlas until the muscles relax. The relaxation of muscles in this manner tends to also allow other misplaced body structure to return to its original position once the buildup of fasciitis is manually released. Moreover, an individual can be taught how to use the method and apparatus of the present invention to thereby maintain correct body structure and relaxed muscles.

12 Claims, 4 Drawing Sheets

METHOD AND APPARATUS FOR BODY WORK

BACKGROUND OF THE INVENTION

1. Technical Field

The present invention relates to a method and apparatus for bodywork and structural integration, and more particularly to a method and apparatus for centering and maintaining the position of the atlas including a method of relaxing and maintaining the relaxation of muscles in the body.

2. Description of Related Art

Numerous methods and tools have been developed over the years to assist with the manipulation of body parts and muscles with the goal of bringing those body parts and muscles back to normal function. The tightness of muscles in the body can result in medical problems for the individual that would not have existed had the individual not had tight muscles in the first place. The techniques for loosening muscles include traditional cross-frictional massage, deep muscle massage, whole body massage, and Rolfing. Chiropractic techniques have also been used for putting vertebrae, etc. back into its correct position.

The problem with all of these techniques is that they do not address the underlying problems that any given individual may have that led to the muscle tightness and/or incorrect body structure, nor do they teach the individual how to maintain relaxed muscles and correct body structure. These methods typically involve the use of excessive force to relax muscles and reposition the body structure. The use of such force results in only temporary relief and requires the use of continuous treatment.

Many of the problems associated with tight muscles and misplaced body structure can be traced to an atlas that is out of alignment. In certain individuals, the atlas has a tendency to rotate as much as approximately one quarter of a turn counterclockwise (as viewed from above) relative to the occipital bone. This rotation of the atlas from its normal position can cause problems such as back pain because it results in a tightening of muscles on the right side of the body which can lead to the tightening of muscles down to the feet and resultant pain in certain parts of the body.

Therefore, a method and apparatus is needed for gently repositioning body structure and relaxing the muscles that caused the improper body structure. The method and apparatus should encourage the natural repositioning of body structure and the natural relaxation of tight muscles. The method should be capable of use by a lay person so that an individual can maintain correct structure and relaxed muscles without continuous visits to a practitioner. The apparatus should be lightweight, inexpensive to manufacture, and should promote the centering and maintenance of a centered position of the atlas on the occipital bone.

SUMMARY OF THE INVENTION

The present invention provides a method and apparatus for obtaining and maintaining correct alignment of body structure. In one embodiment of the invention, a head band is utilized that places light pressure on the erector spinae and sub occipital muscles below the occiput to relax the muscles that caused the counter clockwise rotation and light pressure is maintained to correct the misalignment of the atlas and occipital condyles. The head band can be worn continuously by the user until such time as the atlas will maintain a centered position without assistance. In another embodiment of the invention, the atlas is centered by applying manual gentle pressure to relax the muscles that caused the counter-clockwise rotation. Once relaxed, light pressure is manually applied to correct the misalignment of the atlas and occipital condyles. Gentle pressure can also be applied to the muscles that tightened as a result of the misplaced atlas until the muscles relax. The relaxation of muscles in this manner tends to also allow other misplaced body structure to return to its original position once the buildup of fasciitis is manually released. Moreover, an individual can be taught how to use the method and apparatus of the present invention to thereby maintain correct body structure and relaxed muscles. More details of the invention and embodiments thereof can be found in the detailed description below. This summary of the invention is not intended to be limiting on the scope of the claimed invention.

BRIEF DESCRIPTION OF THE DRAWINGS

The novel features believed characteristic of the invention are set forth in the appended claims. The invention itself, however, as well as a preferred mode of use, further objectives and advantages thereof, will best be understood by reference to the following detailed description of an illustrative embodiment when read in conjunction with the accompanying drawings, wherein:

DETAILED DESCRIPTION OF THE INVENTION

Figure 1:
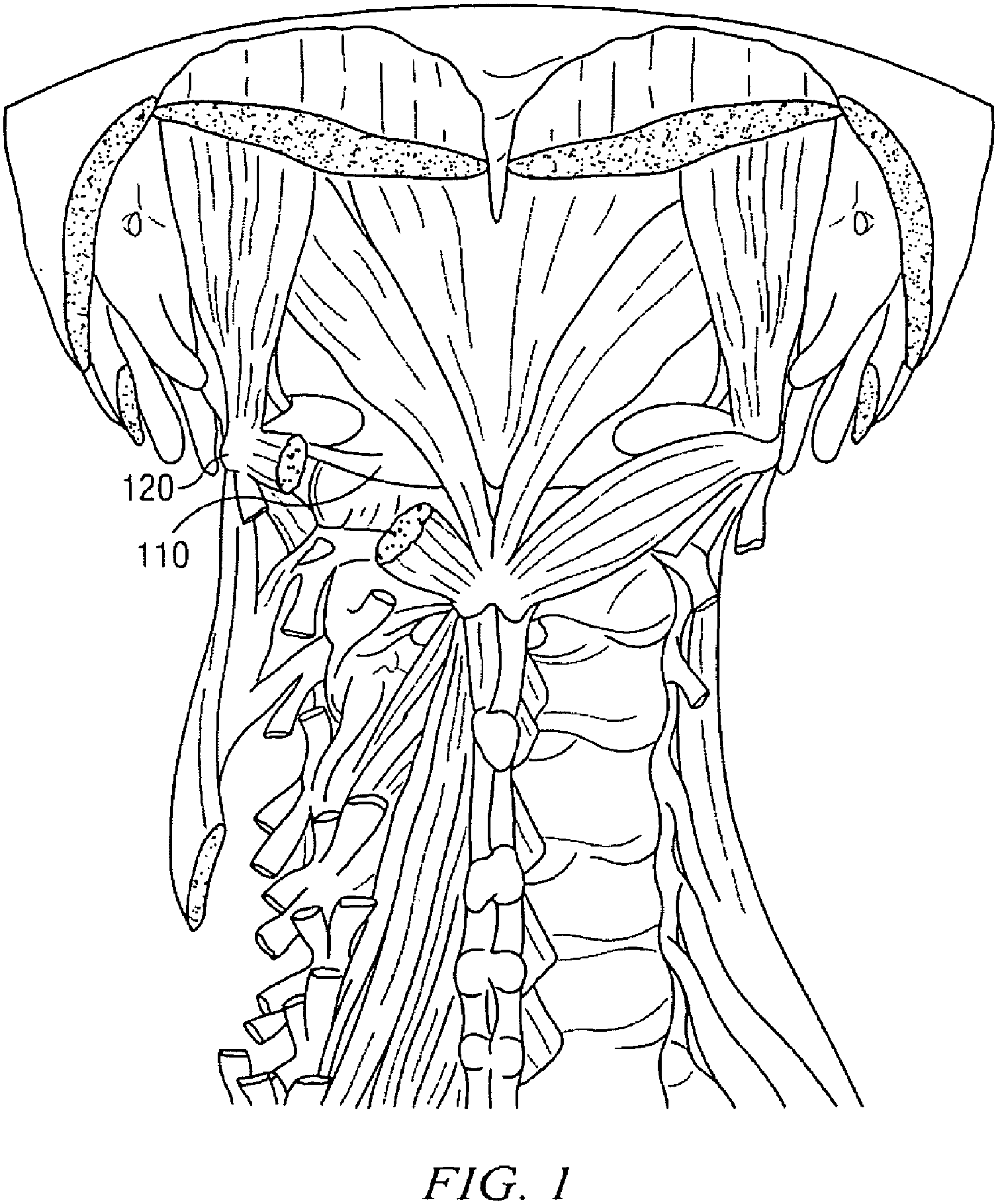
FIG. 1 is a posterior view of the anatomy of the base of the scull and upper portion of the spinal column showing the atlas and muscles surrounding the atlas.

Referring now to FIG. 1, a posterior view of the anatomy of the base of the scull and upper portion of the spinal column showing the atlas and muscles surrounding the atlas is illustrated. A source of many soft-tissue problems such as tight and/or shortened muscles can be traced to misalignment of the atlas 110. The obliquus capitis inferior muscle 120 originates at the transverse process of the atlas 110.

Figure 2:
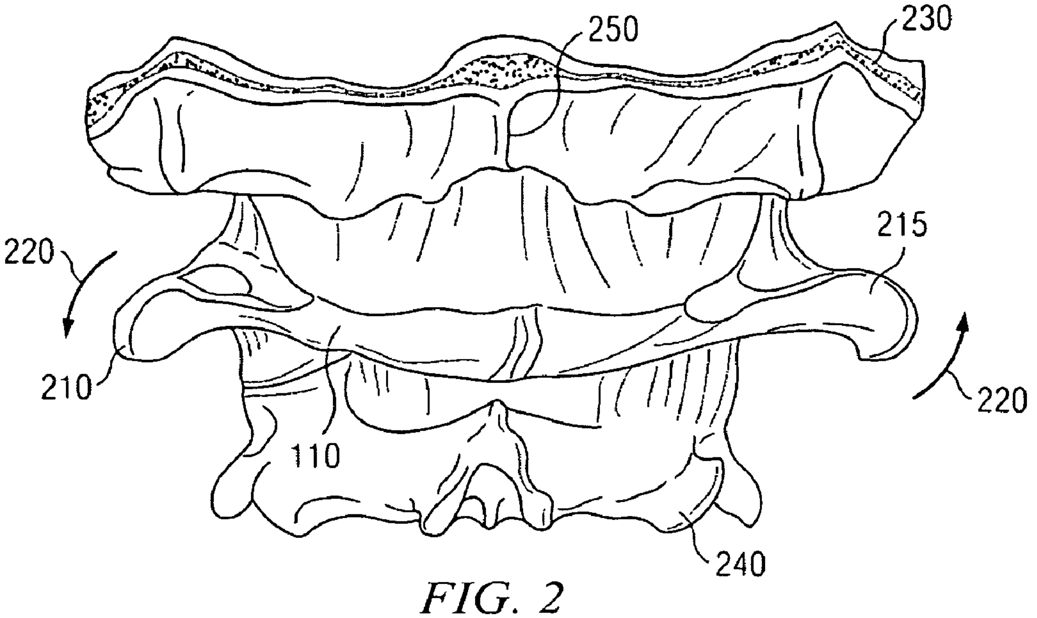
FIG. 2 is a posterior view of the alanto-occipital and alantoaxial joints.

Referring now to FIG. 2, a posterior view of the alanto-occipital and alantoaxial joints is shown. The atlas 110 lies between the occipital bone 230 and the axis 240. In some individuals, the atlas 110 has a tendency to rotate in a counterclockwise direction 220. When the atlas 110 rotates in this manner, the left side transverse process 210 can be felt through the posterior muscles of the neck 120 on the left side of the neck at the base of the scull.

In accordance with an embodiment of the present invention, the atlas can be checked for proper position, and if misaligned, returned to the correct position in the following manner. First, the medial nuchal line 250 on the occipital bone 230 is located with the thumbs. Then the thumbs are moved laterally outwardly approximately ½" to each respective side of the medial nuchal line 250. The thumbs are then moved inferior as the occiput slopes inferior and anterior. The left transverse process of the atlas 210 must be located. This left transverse process can be found at any position from zero degrees counterclockwise rotation, up to ninety degrees counterclockwise rotation, with zero degrees representing the anatomically correct point position, just inferior and medial to the mastoid process of the temporal bone. At that point, the left thumb is placed just medial to the tissue superficial to the left transverse process of the atlas 210. The right thumb is placed on the tissue superficial to the right sub occipital muscles when the sub occipitals are tight. In the event the right sub occipital muscles feel relaxed, the right thumb is positioned on the muscles superficial to the transverse process of the axis to keep the alantoaxial joint from sticking. If the muscles do not feel relaxed, then the muscles should be relaxed, and if the atlas does not begin to rotate after relaxing the muscles and repeating the process above, then L4/L5 should be released as discussed below and the centering process repeated.

To relax the muscles that rotate the atlas counter clockwise 110, light pressure is held on the muscles superficial to the left and right transverse process of the atlas (C1) with the left and right thumbs, respectively, for several seconds. Then the right thumb is lifted. When the right thumb is lifted, a response will be felt at the left thumb if the thumbs are properly positioned. Then the right thumb is pressed down lightly again, and a response should be fell on the left thumb. The right thumb is lifted again and the process is repeated multiple times. As the procedure is continued, the transverse process 210 under the left thumb moves in a clockwise direction. As the transverse process 210 begins to move, the left thumb is kept just medial to the left transverse process 210. The procedure is continued until the transverse process 210 moves just inferior and medial to the mastoid process of the temporal bone.

Once the atlas 110 is centered, the left thumb is pressed lightly such that movement is felt under the right thumb. This procedure ensures that the occipital condyles have properly seated in the superior articular facets of the atlas. Correct positioning will not be realized unless the occipital condyles and the superior articular facets of the atlas are correctly mated. Correct positioning of the atlas 110 can be enhanced by the individual rotating his or her head counterclockwise, holding his or her chin, and leaning his or her head forward. A friend, therapist or partner can also traction the head superiorly to encourage the occipital condyles to seat properly within the superior articular facets of the atlas.

To test whether the atlas 110 is centered, pressing on the left transverse process 210 just inferior the mastoid process results in movement by the right transverse process 215, and vice versa. It is important when realigning the atlas 110 to be patient and to apply light pressure. Applying excessive pressure will cause the muscles to tighten up rather than relax. Although the atlas 110 can be forced into place, this will not result in a lasting improvement due to the tightness in the muscles pulling the atlas 110 back to an un-centered position.

Figure 3:
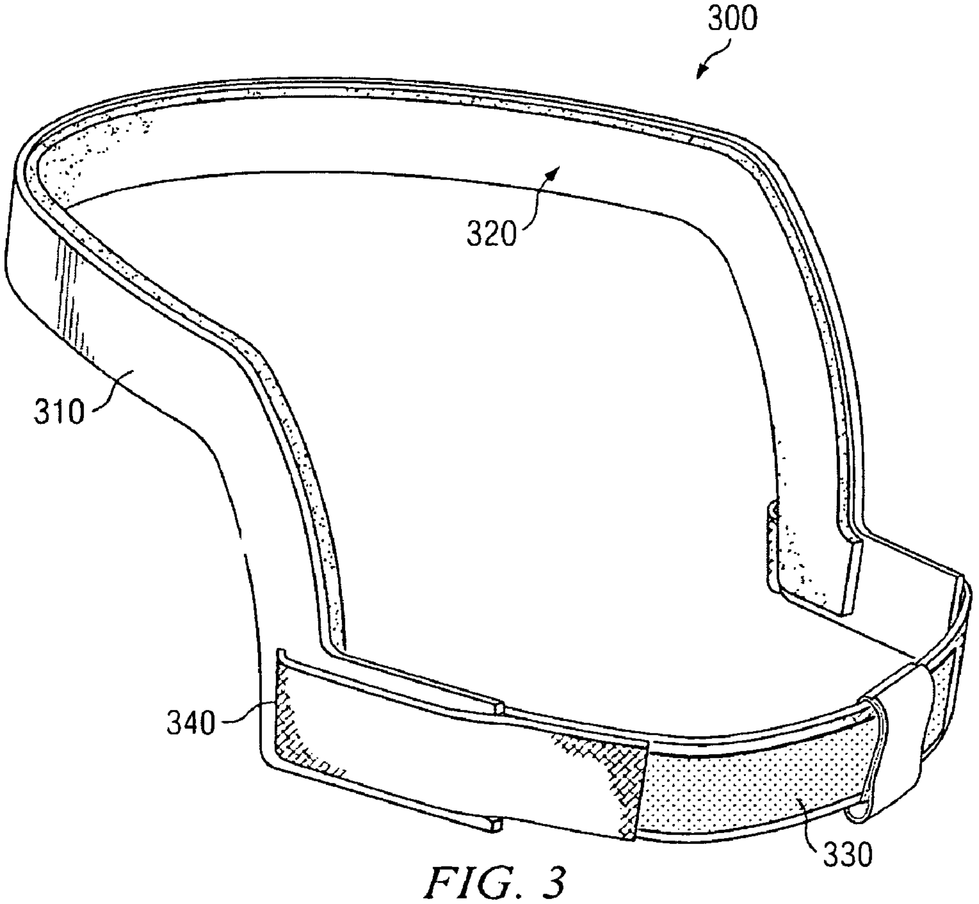
FIG. 3 is a rear perspective view of a head band in accordance with an embodiment of the present invention.

Referring now to FIG. 3, a rear perspective view of a head band in accordance with an embodiment of the present invention is illustrated. The head band 300 may be constructed of a lightweight polyethylene plastic frame 310 or other flexible material. A foam rubber liner 320 may be used to line the inside of the frame 310 to make the band comfortable to wear. An adjustable strap 330 is attached through slots 340 in the frame 310.

Figure 4:
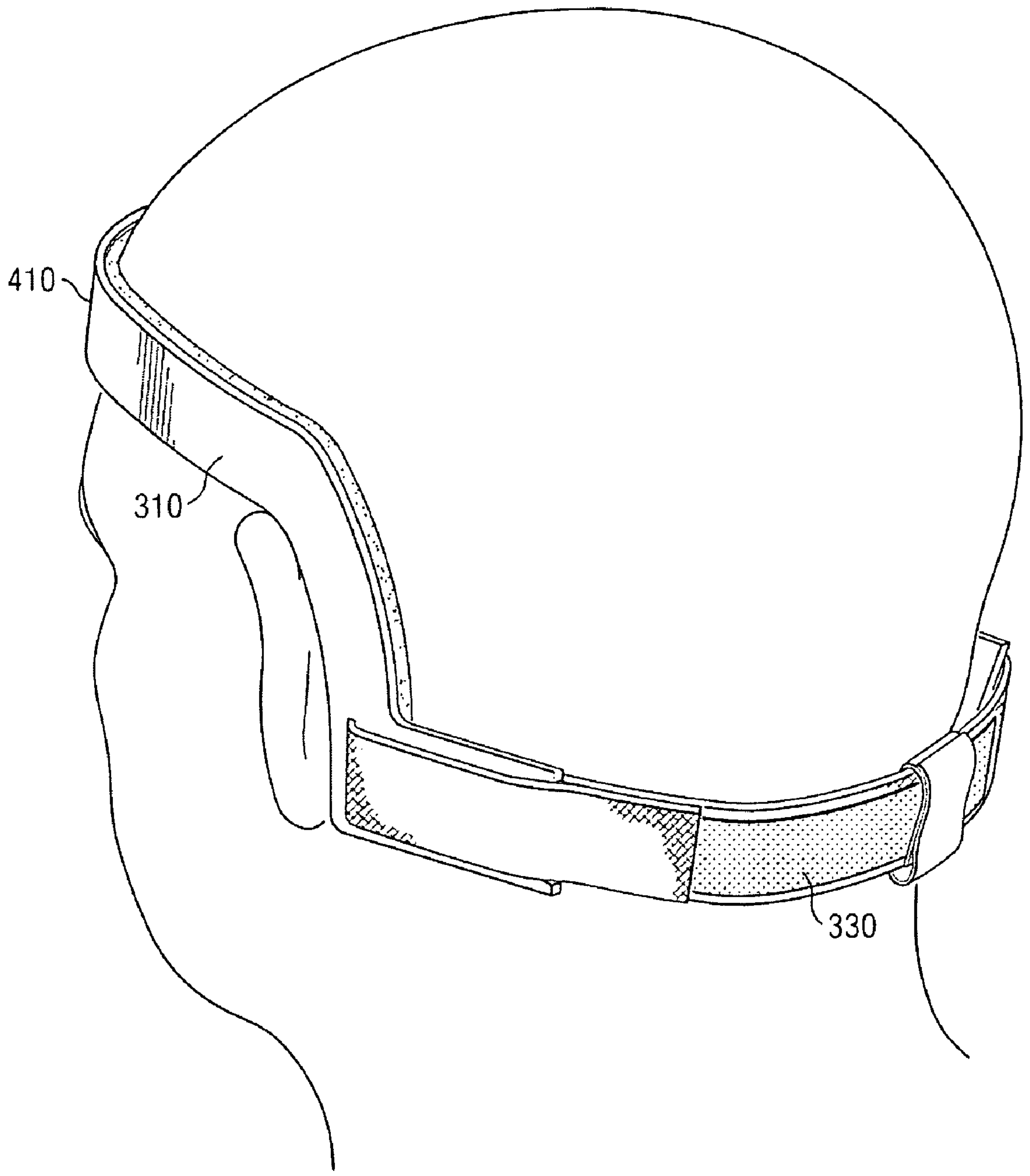
FIG. 4 is a rear perspective view of a head band placed on a user in accordance with an embodiment of the present invention.

Referring now to FIG. 4, a rear perspective view of a head band 300 placed on a user in accordance with an embodiment of the present invention is illustrated. The front portion of the band 410 is placed on the forehead and the adjustable strap 330 is tightened to apply light pressure to the muscles superficial to the atlas 110 at the base of the skull with specific attention to the sub-occipital muscles. The head band 300 may be utilized to either maintain relaxed muscles so the atlas 110 slays centered or to gradually relax the muscles like the sub occipitals and erector spinae to encourage the atlas 110 to return to its anatomically correct position.

The user may need to wear the head band for several days or more initially so that the muscles that hold the atlas 110 in place have time to recondition to hold the atlas 110 in a centered position as well as allowing the erector spinae and sub-occipitals to maintain a relaxed tone and preventing tight muscles from causing an incorrect positioning or counter-clockwise rotation of the atlas. Once the atlas 110 is centered and remains centered without use of the head band 300, the head band 300 may be removed and used again as needed.

Figure 5:
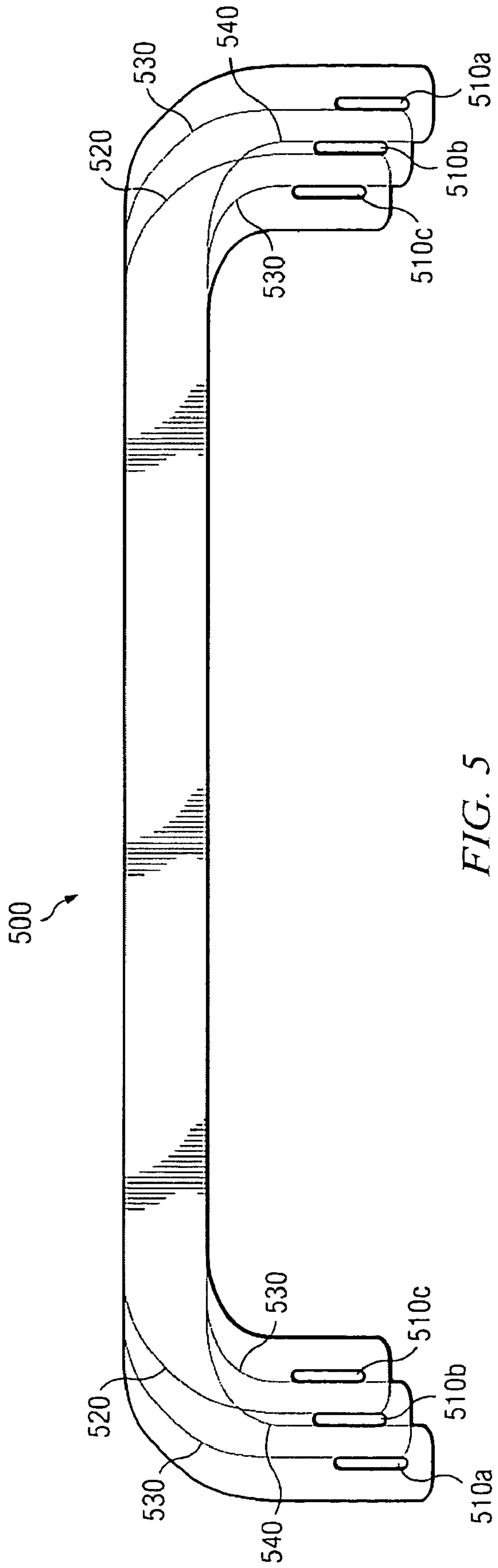
FIG. 5 is a side view of a frame to fit various head sizes in accordance with an embodiment of the present invention.

Referring now to FIG. 5, a side view of a frame to fit various head sizes in accordance with an embodiment of the present invention is illustrated. To cut down on production costs and to prevent the re-ordering of different size head band when one does not fit, the frame 500 can be manufactured as illustrated with three slots 510*a*, 510*b*, 510*c* on each end of the frame 500 to accommodate different head sizes. For the largest size, the user cuts along the longest length lines 540 and attaches an adjustable strap in the longest length slots 510*a*. For the medium size, the user cuts along the medium length lines 530 and attaches an adjustable strap in the medium length slots 510*b*. For the smallest size, the user cuts along the short length lines 520 and attaches an adjustable strap in the medium length slots 510*c*. The head band can then be used in a manner similar to that discussed above with reference to FIG. 4.

Once the atlas 110 is centered, remaining soft tissue of the body can be worked either as part of a whole body treatment or to focus on specific ailments. Although centering the atlas 110 is important, a systematic procedure for checking, repositioning, and relaxing other parts of the body is desirable to help clear and eliminate fasciitis and tight connective tissue and return the body to the normal healthy state. In general, any muscle tissue in the body may be relaxed. When a muscle is "released" or "relaxed," tissue that was once tight, hard or fibrous is returned to its normal soft, pliable, movable or pain free state.

To relax a muscle, the hand or other object is positioned at the muscle "belly" (near a center of the muscle) and the muscle tissue is stretched by applying light pressure. After the initial stretch, some pressure is released and then reapplied. If after approximately 45 seconds, a muscle does not start to stretch, or if a muscle previously stretched becomes tight again, it is possible that the tightness of the muscle has caused a chain reaction resulting in the atlas 110 moving from its centered position. Thus, the atlas 110 can be re-checked and re-centered as necessary and the muscle then re-stretched. It is important when stretching muscular tissue to allow the muscle to stretch gently without forcing the stretch by increasing the pressure. If excessive force is used, this may cause the muscle to rebound back to its original tense state rather than relax.

Generally, it is not necessary to focus on the attachment sites for muscles (called origins and insertions) because once the muscle belly relaxes; the origins and insertions also relax. This is in contrast to other techniques like Neuromuscular Therapy that focus on origins and insertions. Focusing on the muscle bellies is less painful and more productive that other techniques because it allows the body to work with the fascial system instead of fighting against itself and initiating the pain spasm pain cycle. Nevertheless, in severe cases fasciitis may have developed on the insertions, in which case this fasciitis may require manual release directly on the insertions and less frequently on the origins as well.

In cases involving a severe biomechanical deviation from normal (normal is depicted on the Peter Batchen anatomical chart) for a prolonged period of time, it is common that muscle tissue will not completely release during the first session, and therefore, multiple sessions are required. The stretching procedure should be temporarily stopped when a muscle is no longer stretching, and return to that area the following day.

After the atlas 110 is centered, other muscles will release more quickly if L-4 and L5 are released first. However, to avoid excessive turning of the body, the whole body stretching routine using the general stretching procedure discussed above may be accomplished in the order discussed below.

First, with the patient lying down on his or her back, starting about 2½ " below the coracoid process of the scapula, closest to the humerus, the pectoralis major is stretched. After the initial stretch, the breast tissue is palpated. Non-cancerous lumps in the breast can generally be released using the same technique. The entire pectoralis major is palpated to release any fibrous tissue.

Second, the index and middle finger are placed just above the xiphoid process. If soft spongy tissue on the sternum is felt, this tissue must be released gently, because it is extremely tender. Once the spongy tissue is released, the boney surface of the sternum is palpated. It is advisable to work this area several times a day for several days, because it can take several days before complete release can be achieved.

Third, the pectoralis minor is stretched by positioning the hand below the coracoid process of the scapulae and above the external surfaces of the third, fourth and firth ribs.

Fourth, the upper arms are stretched by grasping the biceps below the deltoid tuberosity and maintaining light but firm pressure to initiate a stretch. In the event the upper arms do not release, the pectoralis minor should be released again and another attempt made to release the upper arms. If the pectoralis minor is fully relaxed and the upper arm will stili not relax, the Subclavius muscles and the muscles surrounding T1 & T2 (Thoracic vertebra #1 & #2) should be relaxed. If pectoralis minor will still not completely relax, clear L-4 & L5 (Lumbar vertebra #4 & #5) as explained in the seventh step below. The triceps may be released by grasping the muscle belly and maintaining light but firm pressure.

Fifth, the forearms are palpated to ascertain where the flexor and extensor muscles are light. If the entire forearm is tight, both the extensor retinaculum and the flexor retinaculum must be released. To release a retinaculum, firm pressure is applied until the retinaculum begins to stretch. Once the retinaculum begins to stretch, the stretch is moved toward the proximal end of the retinaculum, and pressure is held to release the fasciitis causing a narrowing of the carpal tunnel and/or the space available to allow free movement of the flexors or extensors. The entire retinaculum should be stretched. The forearms are palpated again and if one area is still tight, the retinaculum directly below the area that is tight is released. If only the anterior forearm is tight, the flexor retinaculum is released. If only the posterior forearm is tight the extensor retinaculum is released. If the forearm is only tight at the posterior upper area, the pectoral is muscles should be released again along with the bicep brachii and triceps muscles. If the forearm remains tight only at the proximal ends near the elbow, the insertions of biceps brachii should be directly released.

Sixth, the Iliotibial tract (IT tract/band) is checked for a relaxed state. If the IT band is tight, the tensor fascia latae must be released. This is accomplished by applying very light pressure to encourage the tensor fascia latae to relax. The tensor fascia latae is a very superficial muscle, and consequently, excessive pressure will press through the tensor fascia latae.

Seventh, with the patient lying on his or her stomach, the muscles surrounding the fourth and fifth lumbar vertebra (L4/L5) are stretched. The L4/L5 vertebras are palpated between the transverse processes of L4 & L5 to feel for depressions. The depressions are pressed simultaneously. When the muscles relax on one side, the pressure is released on the relaxed side. When releasing pressure, movement should be felt on the opposite side. The pressure should be held until the muscles relax on the opposite side and movement is obtained. Once the muscles are completely relaxed, the depressions disappear. If the depressions do not disappear, the above procedure is repeated. It is important during this procedure to release any fasciitis at the iliac crest located bilateral to L5. This is a painful area and can take numerous sessions to clear buildup in this area.

Eighth, the erector spinae is released. Starting with the posterior trapezius at the superior border of the scapula, the iliocostalis, rhomboids, serratus posterior superior and inferior and quadratus lumborum are released. The obliques and transverse abdominis are palpated and released if found to be tight. The longissimus as well as levator scapulae are checked and released if tight. The rotator cuff muscles and serratus anterior are checked and released if tight. If any depressions against the spine are located, the depressions should be removed in the same manner that depressions surrounding L4 and L5 are released as discussed above in the seventh instruction.

Ninth, the piriformis is released. Starting at the muscle belly of the piriformis located on the lateral side of the sacrum, pressure is applied into the muscle belly the thumbs. Both right and left piriformis muscles are released.

Tenth, the muscles and ligaments covering the sacrum are checked for a relaxed state indicated when the sacrum has slight movement. The sacrum is firmly pressed with the heel of the hand, anteriorly. When the pressure is released, the sacrum should move freely on both sides. If no movement is felt, the piriformis and other deep hip rotators should be stretched or released. If the sacrum is still stuck, the hips should be tilted posteriorly and then anteriorly to release the pressure on S1, which is the first of five fused vertebra of the sacrum. If the sacrum is still hung, then the gluteus maximus is checked to ensure that it is fully released. If sacrum is still hung, the patient will need a sacral adjustment by a chiropractor. If depressions are found on the sacrum the depressions should be removed in the same manner any depressions surrounding L4 and L5 are released as discussed above in the seventh instruction.

Eleventh, the superficial pubococcygeus (PC) muscle on coccyx is released. The coccyx is checked for proper angle which is no more that thirty to forty degrees anterior curve. The coccyx is also checked for tenderness. If tender, the PC muscles are released by placing the fingertips just lateral of the genitalia and applying gentle pressure in the superior direction. One can also be instructed and do Kegel exercise to strengthen the PC muscle and release restrictions. If the coccyx is turned laterally or is angled (curved) more than forty degrees anterior or straight in toward the pubis, the angle of the curve may be gradually reduced by internally applying pressure to the coccyx posteriorly, over three or fours separate sessions, until an anterior curve of no more than forty degrees is present. Lessening the degree of the coccyx's anterior curve too quickly may cause side effects like constipation. For a lateral deviation of the coccyx, medial light pressure is applied to correct the lateral deviation so the coccyx is positioned midsagittally.

Twelfth, the illiotibial tract attachment at lateral condyle of tibia is released. Pressure is held on the attachment of the illotibial tract until the tissue relaxes.

Thirteenth, the illiotibial tract (also called IT band) is palpated along its length to check for a soft and relaxed state. If IT band is still tight, the tensor fascia latae should be checked and released as discussed above in the sixth instruction.

Fourteenth, the patellar ligament on anterior tibia is checked and released. The attachment for the patellar ligament on the anterior tibia is pressed and held until the tissue relaxes.

Fifteenth, the hamstrings are checked and released. If the hamstrings are tight, the sacrum is probably hung. In that case, the tensor fascia latae, the piriformis and the sacrum should be released as discussed above in the sixth, ninth, and tenth instructions, respectively. Then the pez anserinus (the attachment of the gracilis, sartorius and semi-tendonitis) is pressed and held. The insertion of the biceps femoris on the lateral side of head of fibula and lateral condyle of tibia is released. Then the hamstrings are held and stretched.

Sixteenth, the calf muscles are checked and released. The entire calf is palpated for tightness. If the medial side is tight, then the flexor retinaculum is released. If the lateral-side is tight, then the superior and inferior peroneal retinaculums are released. If the soleus and gastrocnemius are tight, they are held and released and then the insertions for the hamstrings, IT band and adductors are released. The Achilles tendon is checked, and if tight, the fasciitis on the tendon is released. This will be moderately to severely tender; however the fasciitis must be cleared to relieve pain and tenderness in the area.

Seventeenth, the plantar surface of the foot is checked and released. The foot is positioned in extention with the toes hyper-extended. The muscle tissue on the plantar side of the foot is then released. The lateral and medial side of the foot are also checked and released if tight. With the patient reclining in the supine position, the foot is hyper-flexed. If the muscles on the dorsal side of the foot are tight, or if the toes are pulled up, the inferior extensor retinaculum as well as the muscles deep to the retinaculum are released.

Eighteenth, the atlas is checked and re-centered if necessary. It is common that retinaculum work, due to its painful nature, will cause muscle spasms, causing the atlas to move off center.

Nineteenth, the face is checked and released. Starting above the bridge of the nose, above the eyebrows, starting with the thumbs or middle fingers touching, slide the thumbs or fingers apart until the respective temple area (greater wing of sphenoid bone) is reached. The fingers are slid laterally to the temples. The entire forehead is released in this manner moving one finger or thumb width superiorly each stroke until the hairline is reached. Then again starting at the bridge of the nose, the fingers are slid inferiorly until they reach the sides of the nostrils while using care not to restrict air flow. Then the fingers are slid laterally under the cheek bones (zygomatic bone). The infraorbital foramen is held until the nerve is released. The nerve is released when the tissue superficial to the infraorbital foramen is soft, pliable and pain free.

Twentieth, the thyroid is checked and released. The thyroid is held gently. If a tight ball is felt, the thyroid is held until the connective tissue allows the thyroid to return to a normal size.

Twenty-first, the scalene and tempormandibular joint are released. The middle and anterior scalene is released by holding gentle lateral pressure in the muscle bellies between the connections of the rib and cervical vertebra. Working superiorly, both anterior and middle scalene are gently released. If the posterior scalene is tight, which is unusual, it should be released with a stretch medially. For a patient with TMJ, the scalene should be released to up behind the mandible. Then, the stylomandibular ligament is gently released. The masseter muscle is released and the tempormandibular joint is checked for free movement & pain relief. The mouth is then opened and the tissue at the tempormandibular joint is again released.

Twenty-second, hardness in the abdomen is checked and released. The first layer of muscle tissues in the abdomen is released. The abdomen is checked for any tight or abnormal abdominal tissue. Any tight tissue is held to release. It typically takes three to live sessions to acquire full release of tightness in the abdomen.

Twenty-third, any ovarian cysts are checked and released. If an oval non-spiky cyst is felt just medial to iliacus, the iliacus should be released and the cyst held until connective tissue surrounding ovary is released. Once the ovaries are released, the ovaries typically cannot be fell.

Twenty-fourth, the quadriceps are checked and released. If the quadriceps are tight, the TFL (see step six above) and IT band (see step twelve above) should be released. Then the rectus femoris and other quadriceps muscles as well as patellar ligament are released.

Twenty-fifth, the adductors are checked and released. If the adductors are tight, first release the muscles and ligaments over the sacrum (see step ten above). Then starting mid-thigh at adductors, the adductors are held and released.

Twenty-sixth, the calves are re-checked. If tight, the retinaculum is re-released (see step sixteen above).

Twenty-seventh, the atlas is re-checked and re-centered if necessary as described above.

This completes the general full body treatment in accordance with an embodiment of the invention. The procedure may need to be repeated several times to see lasting results depending on the condition of the patient. However, by using this treatment and applying gentle pressure as instructed above, results are seen much quicker than in other forms of treatment where excessive force is used in an attempt to stretch a muscle or reposition body structure. Moreover, non-professionals can be trained to perform their own corrections, maintenance, and prevention so as to increase the likelihood of success of the treatments described.

The present invention may be used not only as a whole body wellness procedure but also to address specific ailments. Some of the ailments are discussed below, but the principles of centering the atlas and gently relaxing muscles may also help other ailments not specifically listed herein. Common to the treatment of any ailment as discussed below is centering of the atlas and releasing the muscles surrounding the L4 and L5 vertebra. The general procedures discussed above in regard to releasing various muscles can be performed with specific attention paid to certain areas depending on the ailment to be treated.

Arthritis is shortening, thickening and hardening of the connective tissue caused by an imbalance, where the muscles are constantly pulling the joints into themselves. This results in fasciitis buildup on or around the joints and Hat bones. In addition to the general procedures discussed above, particular attention should be given to releasing the fasciitis buildup on or around the joints.

Asthma is a result of excessive tightening of the erector spinae muscles resulting in a tightening of tissue around thoracic vertebra #6 and #7 (T6/T7). This causes the muscle tissue that wraps around the chest to become tight, resulting in a semi-hard knot to arise on the lower ⅓ of the sternum and inflammation of the bronchial tubes. In addition to the general procedures discussed above, particular attention should be given to releasing the muscles around the erector spinae and the sternum. Generally the muscles at T6-T7 will pull the vertebra to one side. These muscles should be held until released. Then the index and middle finger are positioned just above the xiphoid process. If soft spongy tissue on the sternum is felt, this tissue must be released gently, because it is extremely tender. Once the spongy tissue is released, boney surface of the sternum is palpated. In a patient with asthma, the lower ⅓ of the sternum will have a hard knot. The knot can be gently released by holding it. Asthma, bronchitis, and emphysema are all Chronic Obstructive Pulmonary Disorders (COPD). With asthma the knot is on the lower ⅓ of the sternum. With bronchitis the inflammation is bilateral to the sternum in the intercostals. Emphysema is a mechanical issue that cannot be corrected with using the techniques described herein, but the techniques can be used to release tissue so as to improve function so those with emphysema can breathe and function better even with the mechanical problem.

Generally low back pain is caused by an imbalance at the atlas because of improper muscle tension resulting in a counter clockwise rotation of the atlas. After centering the atlas, the muscles surrounding L4-L5 lumbar vertebra should be released as discussed above.

Generally middle back pain is caused by an imbalance at the atlas because of improper muscle tension resulting in a counter clockwise rotation of the atlas. After centering the atlas, the pectoralis major, sternum, pectoralis minor, and erector spinae should be released as discussed above.

Generally, upper back pain is caused by tight muscles surrounding the L4/L5 vertebra causing a misalignment and excessive tightness in the erector spinae muscles. After centering the axis, the muscles surrounding L4-L5 lumbar vertebra should be released as discussed above.

Generally, bones spurs are fasciitis typically located at a tendon where the muscle attaches to bone. This fasciitis builds into a point and pokes into the muscle tissue at the tendon. To release this fasciitis firm pressure is held on the bone spur. The reason that firm rather than gentle pressure must be applied to bone spurs is that bone spurs are hard fasciitis, and hard fasciitis will not release with gentle pressure. This is often very painful, but firm pressure should be held until the spur begins to soften. Typically holding pressure in time spans of 5 to 15 seconds is ideal. If the tissue stops softening, the session should be discontinued and repeated the next day. If possible the fascia should be stretched from the side of the bone spur by pressing around the edges of the bone spur rather than stabbing the muscle by pressing directly into the spur. Once the fascia returns to normal, there will no longer be a sharp pointed substance, and the pain will subside.

Breast pain and fibrocystic breast disease are caused by tight or semi hard connective tissue or fiber cystic build up in the breast tissue, caused by excessive tension in the pectoralis major or pectoralis minor.

Bunions are caused by too much tension at the first metatarsal phalangel joint at the big toe resulting in fasciitis buildup around the joint which gradually increases and displaces the joint medially and causes pain and discomfort. The retinaculum should be released as well as the fasciitis buildup at the first metatarsal phalangel joint, by holding firm pressure. Firm pressure is needed because bunions and buildup at the first metatarsal are generally hard fasciitis, and hard fasciitis will not release with gentle pressure. This procedure is painful during the first few sessions, but the tissue will eventually start to soften and return to the normal state. Generally, 4 to 12 weeks of daily treatment is required for the foot to return to normal. The muscles on the front back and sides of the bunion should be relaxed as well.

Carpal tunnel syndrome occurs as a result of the flexor muscles being chronically tight. This causes tendon inflammation that spreads to the retinaculum further decreasing the size of the carpal tunnel. This condition can be treated by releasing the pectoralis major, breast tissue, sternum, pectoralis minor, upper arms, and wrist retinaculum. These procedures typically must be repeated for 6 to 10 days to resolve the carpal tunnel syndrome.

Drop foot is caused by chronic tension in the retinaculum(s) around the feet as well as the soft tissue around, above and below the ankle resulting in nerve compression and dysfunction. Fasciitis buildup in this area should be released along with the retinaculum of the feet. Typically the drop foot condition will resolve in 3 to 5 days. If gouty arthritis is a factor, all the crystals in the foot must be dissolved by pressing firmly, holding and waiting. This can take several weeks. If neuropathy is present, retinaculum(s) as well as muscle tissue in the foot should be released on a daily basis.

Endometriosis, painful menstrual cycles, and uterine fibroids are all caused by inflamed connective tissue as well as the tissue of the uterus and or cervix, fibroids are just fibrous tissue that is chronically inflamed and typically all as a result of the sacrum being hung. The conditions can be corrected by releasing the piriformis, the sacrum, sacrum depressions, and the superficial pubococcygeus muscle on coccyx, the illiotibial tract attachment at the lateral condyle of tibia, the IT band, and any hardness in the abdomen.

Fibrocystic Breast Diseases is caused by excessive inflammation in the pectoralis muscles and fibrocystic buildup in the breast tissue. This condition can be corrected by performing the general whole body procedure and paying special attention to pectoralis major, pectoralis minor, serratus anterior.

Fibromyalgia is caused by muscle tissue which is hypertonic or hyper tight but not contracted. Thus, the muscles are tight, causing fasciitis in the muscle tissue, but the muscles are not pulling the joint into itself as with arthritis. This condition can be corrected by using the general whole body procedure as well as holding the muscle tissue to release the fibrocystic buildup. For areas that cannot be reached when performing the procedure, one may lie on a tennis ball at the tender area until the tenderness subsides indicating that the fibrocystic buildup has been released.

Foot Pain is generally caused by L4-L5 rotation. This condition can be relieved by releasing L4-L5, the tensor fascia latae, the piriformis, sacrum, the deep hip rotators, the gluteus maximus, the PC muscles, sacral depressions, IT band insertion at lateral condyle of tibia, IT band, patellar ligament on anterior tibia, hamstrings, calves, retinaculums of the foot, and plantar (bottom) surface of the foot as described above in steps 7, 6, 9, 10, 11, 12 above. If the tissue is tender when pressed into, the foot may be placed on top of a golf ball, rolling the ball over the entire bottom surface of the foot to release the tender areas. It is important to exercise patience during this process and continue movement until the tenderness in the area subsides. This procedure should be continued for several treatments until the patient can stand on the golf ball with no pain. If the foot pain returns, clear the sacrum by applying pressure anteriorly with fingertips at S3 & S4 or apply pressure to this area by positioning a tennis ball on the sacrum and having the patient lie on the tennis ball. The PC muscle should be strengthened by performing Kegel Exercises. This will help hold the sacrum in proper alignment and reduce the likelihood for the sacrum to hang. The TFL and piriformis should also be released for several days to prevent the sacrum from hanging.

Forward Head Posture is caused by muscle contracture as a result of an imbalance at the occiput-C1 and L4-L5 tension, erector spinae muscles, pectoralis muscles and scalenes. This condition can be corrected by centering the atlas and releasing the scalene as discussed above in steps 7, 8, 1, 3, respectively.

Hammer Toe is caused by too much tension of the flexors and extensors of the toes at the metatarsal phalangel joints. This condition can be corrected by releasing the IT Band, retinaculums, muscle tissue flexors and extensors of the feet and fasciitis build up in the joints of the toes by holding firm pressure on the hard fasciitis buildup on and/or around the joints as discussed above in steps 12, 13, 16, respectively.

Headaches are generally caused by an Occiput-C1 imbalance resulting in L4-L5 issues, causing excessive tightness in the erector spinae (specifically longissimus at the mastoid process), which results in tension and fasciitis buildup on the occipitalis muscles that causes pain to encircle the head. Headaches can be resolved by releasing the occipitals, the temporalis, the frontalis, and the sinuses. The occipital muscles may be released by placing the thumbs on the lateral edges and releasing any knotted muscles. The temporalis may be released by using the fingers or thumbs to relax the muscles from the occipitals working anteriorly through the temporalis. To release the frontalis, starting at the midsagittal position, at the hairline, the muscles of the forehead down to the bridge of the nose are relaxed. To release the sinuses, starting at the bridge of the nose, the tissue just lateral to the sides of the nostrils is pressed and the fingers or thumbs are moved interiorly to the cheek bones and then laterally under the cheek bones. The infraorbital foramen is held until all tissue is released. Migraines may be resolved by first determining which direction C3 is being pulled and then working the muscle on that side by gently holding the muscle. The muscle should be held until it releases, at which point C3 should return to the correct position. If not, the procedure should be repeated. The scalene should also be released.

Hip pain is caused when the muscles and ligaments are tight and pull the ball and socket into the hip joint too tightly. Usually the piriformis is the main problem. However, the erector spinae, piriformis, sacrum, deep hip rotators, gluteus maximus, superficial PC muscle on Coccyx, illiolibial tract insertion at lateral condyle of tibia, and IT band should be released as discussed above in steps 8, 9, 10, 11, 12, 6, respectively. Additionally, the hip should be checked for full circumduction of the hip joint. If the hip does not exhibit full circumduction, torque can be placed on the joint in opposition to the natural wrap to unwind the ligaments. These procedures generally must be repeated for several weeks to resolve hip pain. Patients can use a tennis ball to release the buttocks muscles by placing the tennis ball on the muscle belly of the gluteus maximus and lying on the ball until the tissue softens.

Ingrown toenails are a result of hard fibrous tissue on the sides of the nail bed as a result of flexor extensor tension deforming the nail. This condition can be corrected by releasing the connective tissue on the side of the toe paying particular attention to the areas around the nail bed. This should be done three times a day for several weeks and then once a day for 6 to 12 weeks in which time the nail will begin to return to normal form.

Irritable bowel syndrome (IBS) is the result of inflammation of the connective tissue in the abdominal cavity resulting in compression and restriction of the bowel. This can be corrected by releasing the abdomen. The first layer of muscle tissues in the abdomen is released. Any tight or abnormal abdominal tissue is released by holding. Generally, patients with IBS tend to exhibit an iliacus muscle that is inflamed and lender. In that event, the connective tissue two inches medial to the iliacus in the pelvic cavity should be released during the first session. Then the transverse abdominis, internal and external obliques, and the connective tissue surrounding the stomach, bowel and kidneys is released. The abdomen typically takes three to five sessions to acquire full release. In connection with IBS, the sacrum, deep hip rotators and gluteus maximus should also be released.

Knee Pain generally results from too much compression on the knee as a result of tendonitis around the knee or muscular compression where the muscles are pulling the joint into itself. This condition can be resolved by releasing the hamstrings, illiotibial tract attachment at lateral condyle of tibia, IT band, patellar ligament on anterior tibia, and fasciitis on the ligaments on the medial or lateral side of the knee.

Menstrual discomfort is typically caused by a retention of fluid in the uterus that has inflamed connective tissue in an around the uterus and cervix. The swelling puts pressure on the connective tissue and causes pain. This condition can be corrected by releasing the internal and external obliques, the transverse abdominis, and the connective tissue in the pelvic abdominal region. All tissue in the uterine area should be released by using gentle but firm pressure in the uterus area after ensuring the sacrum is clear and the person is not pregnant. Because releasing the uterine area commonly elicits a painful response, it should be done in stages and can take 3 to 7 days. Eliciting prolonged pain can cause a rebound tightening of the overall body and therefore is counter productive. All hard or abnormal feeling tissue around the uterus and pelvic cavity including uterine fibroids should be released.

Neck pain can be resolved by releasing the scalene and checking for TMJ. Additionally, the muscles surrounding L4-L5 and the erector spinae should be released.

Neuropathy is generally caused by inflamed retinaculum(s) as a result of pressure from enlarged tendons putting too much pressure on the nerves creating loss of sensation or pain. This can generally be corrected by releasing the retinaculum(s), muscle tissue and tendons as, as well as releasing the affected muscle tissue that is tight, inflamed and releasing excessive fasciitis buildup around the joint.

Ovarian cysts are generally caused by tight or inflamed connective tissue enveloping the ovaries as a result of inflammation of iliacus which is caused by sacrum being hung. This condition can be resolved by releasing the IT tract/band, the tensor fascia latae, the sacrum, deep hip rotators, gluteus maximus, sacrum, superficial pubococcygeus muscle on Coccyx, and the abdomen. An ovarian cyst will be found one to three inches inferior to the anterior superior iliac spine and will be imbedded in the inflammation around the iliacus. Releasing the sacrum will allow the iliacus to relax and light gentle pressure will release the tissue surrounding the ovaries releasing the ovarian cyst. Typically the ovarian cyst will release the first day. However, this procedure should be repeated daily for three days to ensure the inflammation in the pelvic cavity is removed.

Parkinson's is brought on by compression of the brachial nerve plexus and excessive fasciitis buildup on the scalenes. This condition can be corrected by using the general whole body procedure, paying special attention to the scalenes and excessive tension in the upper body, arms and hands. Depending on the buildup on the scalenes, it could take quite a few sessions to completely release the scalenes and arms.

Planter fasciitis is caused by fascia buildup on the plantar surface of the foot because of excessive tension in the soleus, gastrocnemius muscles, adductors and hamstrings as a result of a stuck sacrum. This condition can be resolved by releasing the IT tract/band, the tensor fascia latae, the piriformis, the sacrum, deep hip rotators, hamstrings, retinaculums. Then release muscle tissue on plantar side of the foot and the lateral and medial side of the fool, following release if pain returns to the plantar area of the foot, the sacrum should be released. A special effort should be made to keep the TFL, IT band, and piriformis relaxed. This problem usually requires regular work two or three times each week for the first couple of weeks.

Prostatitis is caused by inflammation of the prostate gland caused by the sacrum being stuck, inflammation of the iliacus and the pubococcygeus (PC) muscle. This condition can be corrected by releasing the IT tract/band, the tensor fascia latae, the sacrum, deep hip rotators, gluteus maximus, piriformis, sacrum depressions, superficial pubococcygeus (PC) muscle on Coccyx, and abdomen. Kegel exercises should be performed regularly.

Rheumatoid arthritis is caused when the muscles are continually contracted and pulling into the joint resulting in destruction of the articulating cartilage as well as fasciitis buildup on and around the joint. A full body procedure should be performed, paying particular attention to hard fasciitis that feels like bone and fasciitis buildup on the muscles around each affected joint, especially the rotator cuff muscles and the tendons around the knee and hip joints. Tissue around the fingers and toes should be slowly and gently released and the patient should stretch the fingers and toes every day to increase mobility and use.

Scoliosis is caused by abnormal muscle tension, causing lateral deviation of the spine as a result of atlas occipital and L4-L5 imbalance resulting in excessive tension of the erector spinae muscles. This condition can be corrected by performing a full body procedure paying particular attention to the erector spinae.

Thoracic outlet syndrome is caused by compression of the brachial plexus at the scalenes, first rib, and clavicle. A full body procedure should be performed with particular attention to the scalene, rotator cuff muscles, biceps brachii, rhomboids, posterior superior and inferior serratus, latissimus dorsi, and pectoralis minor. While positioning the hand below the coracoid process of the scapulae and above the external surfaces of the third, fourth and firth ribs, this tissue is released. The pectoralis major and breast tissue are also released.

Those skilled in the art should understand that the previously described embodiments of the METHOD AND APPARATUS FOR BODYWORK AND STRUCTURAL INTEGRATION are submitted for illustrative purposes only and other embodiments thereof are well within the scope and spirit of the present invention. Although the present invention has been described in detail, those skilled in the art should understand that they can make various changes, substitutions, and alterations herein without departing from the spirit and scope of the invention in its broadest form.

What is claimed is:

1. A method for body work, comprising the following steps:

- checking an atlas to ensure that said atlas is in a centered position;
- responsive to a finding that said atlas is not in said centered position during said step of checking, centering said atlas by applying gentle pressure to an area on a neck over said atlas, holding gentle pressure for a period of time, and releasing pressure and continuing said step of applying gentle pressure, holding gentle pressure for a period of time, and releasing pressure until said atlas is in said centered position;
- relaxing at least one tight muscle by applying gentle pressure to a belly of said muscle holding gentle pressure for a period of time, and releasing pressure and continuing said step of applying gentle pressure, holding gentle pressure for a period of time, and releasing pressure until said muscle is relaxed; and
- re-checking said atlas to ensure said atlas is still in a centered position and re-centering said atlas if it has moved from said centered position.

2. The method of claim 1 wherein said step of checking comprises feeling said neck near a base of a skull to determine if a muscle feels hard.

3. The method of claim 2 wherein said step of centering comprises applying gentle pressure with a finger on a first side of said neck and feeling a response on a second side of said neck.

4. The method of claim 3 wherein said step of centering comprises placing a first thumb on said first side of said neck over said atlas and placing a second thumb on said second side of said neck over said atlas, holding light pressure on both first thumb and second thumb, releasing first thumb and feeling a response under said second thumb, holding light pressure on said first thumb again and feeling a response under said second thumb, and repeatedly holding light pressure and releasing said first thumb while keeping said second thumb over a transverse process of said atlas until said transverse process moves approximately inferior to a mastoid process on an occipital bone.

5. The method of claim 4 further comprising the step of verifying said centered position by pressing on said second side of said neck over said transverse process approximately inferior to said mastoid process and feeling movement on said first side of said neck over a second transverse process approximately inferior to a second mastoid process.

6. The method of claim 4 wherein said step of centering further comprises rotating a head counterclockwise, holding a chin and leaning said head forward.

7. The method of claim 1 further comprising the step teaching a user how to perform said steps on self.

8. An apparatus for assisting in obtaining and maintaining a centered atlas comprising a flexible frame with a front portion for placement on a forehead of a user and first and second terminal ends configured such that when said flexible frame is placed on a head of said user, said first terminal end is located behind a first ear near a base of a skull of said user and said second terminal end is located behind a second ear near a base of a skull of said user; and a strap attached to said first and second terminal ends of said flexible frame, wherein when said flexible frame with said strap are placed on a head of said user, said strap applies light pressure to said atlas that promotes centering of said atlas if not centered and helps maintain a centered position of said atlas after said atlas is centered, said flexible frame further comprising a plurality of flexible frames, said plurality of flexible frames are different sizes and have attachment means on said first terminal end and attachment means on said second terminal end of each said flexible frames.

9. The apparatus of claim 7 wherein said flexible frames comprise a polyethylene plastic and a padding attached to an inner surface of said flexible frames for providing a comfortable surface to mate with said head.

10. The apparatus of claim 7 wherein said frames is constructed such that a user may cut said frames to fit a particular head size.

11. The apparatus of claim 7 wherein said frames comprise at least two slots for attachment of said strap.

12. The apparatus of claim 7 wherein said strap is adjustable such that said user can vary a pressure applied by said strap to said atlas.

* * * * *